United States Patent
Yonehara et al.

(10) Patent No.: US 7,871,789 B2
(45) Date of Patent: Jan. 18, 2011

(54) METHOD FOR ASSAYING GLYCATED ALBUMIN

(75) Inventors: Satoshi Yonehara, Kyoto (JP); Norio Imamura, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 239 days.

(21) Appl. No.: 12/084,003

(22) PCT Filed: Oct. 27, 2006

(86) PCT No.: PCT/JP2006/321547
§ 371 (c)(1),
(2), (4) Date: Apr. 23, 2008

(87) PCT Pub. No.: WO2007/049762
PCT Pub. Date: May 3, 2007

(65) Prior Publication Data
US 2009/0142787 A1    Jun. 4, 2009

(30) Foreign Application Priority Data
Oct. 27, 2005    (JP) .............................. 2005-313151

(51) Int. Cl.
*C12Q 1/37*    (2006.01)
(52) U.S. Cl. ........................................................ 435/23
(58) Field of Classification Search ................... 435/14, 435/23
See application file for complete search history.

(56) References Cited

U.S. PATENT DOCUMENTS

| | | | |
|---|---|---|---|
| 5,712,138 A | 1/1998 | Kato et al. | |
| 5,789,221 A | 8/1998 | Kato et al. | |
| 6,033,867 A | 3/2000 | Kato et al. | |
| 7,235,378 B2 * | 6/2007 | Yonehara | 435/14 |
| 7,250,269 B2 * | 7/2007 | Kouzuma et al. | 435/25 |
| 2005/0101771 A1 * | 5/2005 | Kouzuma et al. | 530/395 |

FOREIGN PATENT DOCUMENTS

| | | |
|---|---|---|
| JP | 7-041417 | 2/1995 |
| JP | 7-289253 | 11/1995 |
| JP | 8-154672 | 6/1996 |
| JP | 10-279447 | 10/1998 |
| JP | 2000-017173 | 1/2000 |
| WO | 97/20039 | 6/1997 |
| WO | 02/061119 | 8/2002 |

OTHER PUBLICATIONS

Abstracts of Annual Meeting in Fiscal 2000 of the Society for Biotechnology, Japan (partial English translation).
Wikström, et al., "DNA recovery and PCR quantification of catechol 2,3-dioxygenase genes from different soil types", Journal of Biotechnology, vol. 52, No. 2, Dec. 10, 1996, pp. 107-120, XP004095278, ISSN:0168-1656.

* cited by examiner

*Primary Examiner*—Ralph Gitomer
(74) *Attorney, Agent, or Firm*—Hamre, Schumann, Mueller & Larson, P.C.

(57) ABSTRACT

An albumin denaturing agent for digesting an albumin by a protease efficiently is provided. The albumin denaturing agent contains quaternary ammonium having a hydrocarbon group with a carbon number of 12 or more, or a salt of the quaternary ammonium. The albumin in a sample is digested by the protease in the presence of the albumin denaturing agent, a glycated part of the thus obtained albumin digestion product and a FAOD effect a reaction, and a redox reaction between the glycated part and the FAOD is measured, thereby determining a ratio (GA (%)) of the glycated albumin of the glycated albumin with respect to the albumin.

4 Claims, 1 Drawing Sheet

METHOD FOR ASSAYING GLYCATED ALBUMIN

TECHNICAL FIELD

The present invention relates to an albumin denaturing agent.

BACKGROUND ART

A glycated albumin (GA) in a blood cell reflects a history (of about two or three weeks) of an in-vivo blood glucose level, and thus is used as an important indicator for diagnoses, treatment and the like of diabetes. A glycated albumin is an albumin whose an $\epsilon$-amino group of a lysine residue is glycated, and an amount (%) thereof is represented by a ratio (%) of the glycated albumin amount with respect to a total albumin amount.

As a method for assaying the glycated albumin, high performance liquid chromatography (HPLC) and the like are exemplified generally, but as a simple and low-cost method, the following enzymatic method is utilized practically. In this method, firstly, a fructosyl amino acid oxidase (hereinafter, referred to as a "FAOD") is allowed to act on a glycated part of the albumin, thereby generating hydrogen peroxide. An amount of this hydrogen peroxide corresponds to a glycation amount of the albumin. Further, a peroxidase (hereinafter, referred to as a "POD") and a chromogenic substrate that develops a color by oxidation are added to this reaction liquid, so as to effect a redox reaction between the hydrogen peroxide and the chromogenic substrate with the POD as a catalyst. Then, the glycation amount of the albumin is obtained by measuring a chromogenic level of the chromogenic substrate, so that a ratio of the glycated albumin (hereinafter, also referred to as a "GA (%)") can be calculated from the glycation amount and the total albumin amount.

As described above, since the glycated albumin is characterized by the glycation of the $\epsilon$-amino group of the lysine residue, it is desired that the FAOD acts on the glycated lysine residue efficiently. However, this FAOD is not likely to act directly on a protein, and generally, a digestion product of the albumin is prepared by protease treatment so that the FAOD is allowed to act thereon.

However, the albumin in a blood sample is different from an albumin as a purified reagent in that various substances, for example, bilirubin, a lipoprotein and the like bind thereto, so that it is difficult to obtain a fragment on which the FAOD is likely to act from protease treatment. Thus, when assaying an albumin in a sample such as a serum and a blood plasma, it is necessary to add a large amount of the protease into the sample so as to raise reactivity (Patent Document 1), but this causes problems as listed below.

An enzyme and the like in other reagent used for assaying the glycated albumin are deactivated by the presence of the large amount of the protease.

In the case where the large amount of the protease is contained in a reagent, when only a slight part of the reagent contaminates other assaying reagent, an enzyme and an antibody in the other assaying reagent are deactivated, and the other assaying reagent cannot be used.

A protease solution with a high concentration is necessary for adding the large amount of the protease, but the protease is autolyzed so as to degrade the stability.

In the case of seeking to assay in a dry system, for example, preparation of a protease solution with a high concentration that is necessary for preparing a specimen is difficult.

High cost is required for using the large amount of the protease.

Patent document 1: WO 2002/061119 pamphlet

DISCLOSURE OF INVENTION

Problem to be Solved by the Invention

In the light of the above-described problems, it is an object of the present invention is to provide an albumin denaturing agent for digesting an albumin by a protease efficiently.

Means for Solving Problem

The present invention is characterized by an albumin denaturing agent containing quaternary ammonium having a hydrocarbon group with a carbon number of 12 or more, or a salt of the quaternary ammonium.

The present invention is characterized by a method for digesting an albumin in a sample by a protease, which is characterized in that protease treatment is performed with respect to the sample in the presence of the albumin denaturing agent of the present invention.

Moreover, the method for assaying glycated albumin of the present invention includes: a step of digesting the albumin in the sample by a protease; a step of allowing a glycated part of the obtained albumin digestion product to react with FAOD; and a step of determining a ratio of the glycated albumin in the albumin by measuring the redox reaction of the glycated part and the FAOD, wherein the protease treatment is performed with respect to the sample in the presence of the albumin denaturing agent of the present invention in the step of digesting the albumin.

Incidentally, in the present invention, the "albumin" means both of a glycated albumin and a non-glycated albumin.

Effects of the Invention

Since an albumin can be denatured by using the albumin denaturing agent of the present invention, though the mechanism is not known, the albumin can be digested efficiently by conducting protease treatment in the presence of the albumin denaturing agent. Thus, for example, the albumin digestion can be realized sufficiently with a small amount of the protease, and the problems that are caused by using a large amount of the protease in conventional cases can be solved. Therefore, according to the albumin digesting method and the glycated albumin assaying method of the present invention using such an albumin denaturing agent, it is possible to assay the glycated albumin more efficiently than in the conventional method, and these methods are significantly useful in the medical field such as diagnoses, treatment and the like of diabetes. Moreover, the inventors of the present invention have found, for the first time, that quaternary ammonium having a hydrocarbon group with a carbon number of 12 or more or a salt thereof can denature the albumin as described above, whereby the digestion of the albumin can be performed efficiently by the protease. Thus, the albumin denaturing agent of the present invention containing the above-described quaternary ammonium is a significantly useful reagent in the medical field as described above.

DESCRIPTION OF THE INVENTION

Figure 1:
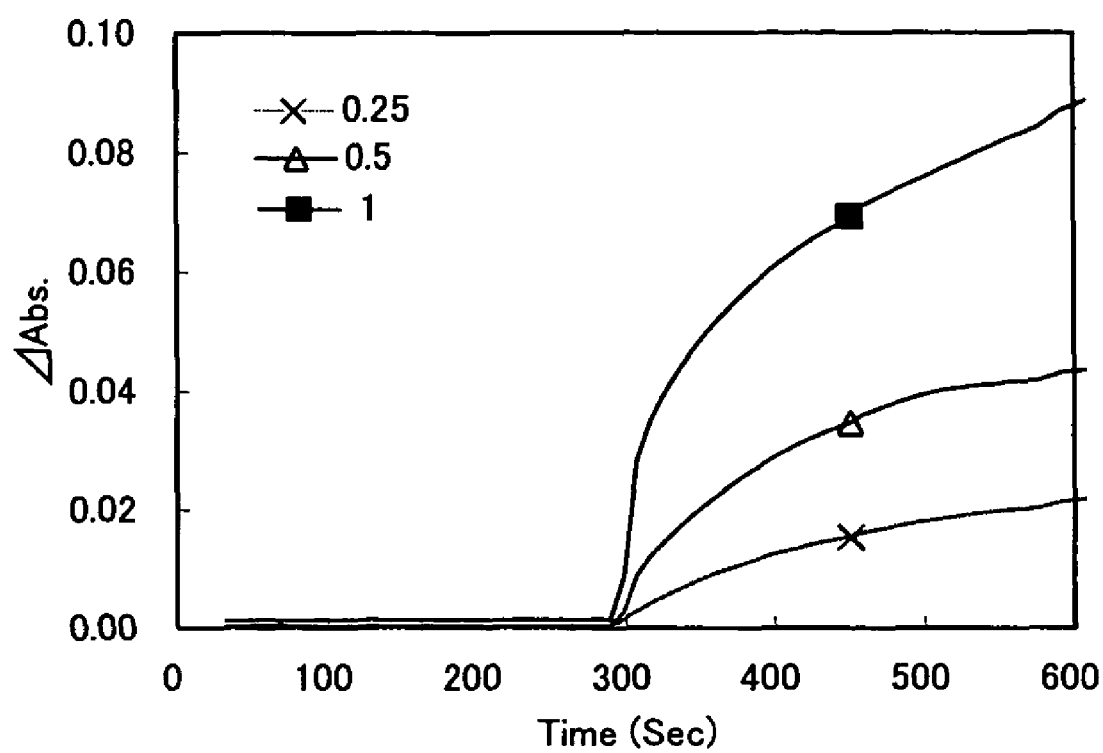
FIG. 1 is a graph showing a change of absorbance that represents a degree of digestion of albumin with time in the examples of the present invention.

The albumin denaturing agent of the present invention contains quaternary ammonium having a hydrocarbon group with a carbon number of 12 or more or a salt thereof (hereinafter, both of them are referred to also as "quaternary ammonium").

The carbon number of the hydrocarbon group may be 12 or more, preferably 14 or more, and more preferably 16 or more. Moreover, an upper limit of the carbon number is not limited particularly. For example, the hydrocarbon group with the carbon number of 14 to 18 is preferable. Further, the albumin denaturing agent of the present invention may contain a mixture of quaternary ammonium having a hydrocarbon group with a hydrocarbon number of 12 or more or salts thereof. For example, the albumin denaturing agent of the present invention preferably includes an albumin denaturing agent that contain a mixture of quaternary ammonium having a hydrocarbon group with a carbon number of 14 or more or salts thereof.

The hydrocarbon group may be, for example, a linear or branched alkyl, a linear or branched alkyl having a substituent, aryl having a substituent or the like. The substituents may be the same or different, and may be a halogen, linear or branched alkyl, phenyl, hydroxy, linear or branched $C_1$ to $C_6$ alkoxy, for example. The aryl is phenyl or cyclohexyl, for example. Moreover, instead of these, linear or branched-chain alkyl carbonyl.

Specific examples of the quaternary ammonium include stearyltrimethylammonium chloride, cetyltrimethylammonium bromide, hexadecyltrimethylammonium bromide, benzalkonium chloride ($C_6H_5$—$CH_2$—$N^+(CH_3)_2$—$RCl^-$; $R=C_8H_{17}$ to $C_{18}H_{37}$), benzyldimethyltetradecylammonium chloride, benzethonium chloride (($CH_3)_3C$—$CH_2$—$C(CH_3)_2$—$C_6H_4$—$O$—$CH_2$—$CH_2$—$O$—$CH_2$—$CH_2$—$N^+(CH_3)_2$—$CH_2$—$C_6H_5Cl^-$), myristyltrimetylammonium bromide, coconut amine acetate ($RNH_2 \cdot CH_3COOH$; $R=C_8$ to $C_{18}$), lauryltrimethylammonium chloride and the like. These compounds may be used alone or in combination of two kinds or more.

The albumin denaturing agent of the present invention may contain at least the above-described quaternary ammonium. The albumin denaturing agent may be constituted only of the quaternary ammonium, and further may contain another compound. As described above, in the present invention, the albumin denaturing agent that contains another compound besides the above-described quaternary ammonium or the salt thereof also is denoted as an albumin denaturing composition of the present invention. Examples of the other compound include: chelating agents such as ethylenediaminetetraacetic acid (EDTA), trans-1,2-diaminocyclohexane-N,N,N',N'-tetraacetic acid (CyDTA), O,O'-bis(2-aminoethyl)ethylene glycol-N,N,N',N'-tetraacetic acid (EGTA), diethylenetriaminepentaacetic acid (DTPA); carboxylic acid such as acetyl tryptophan; buffer agents such as sulfonate buffer including MOPS, PIPES, MOPSO and EPPS. They may be used alone or in combination of two kinds or more.

Forms of the albumin denaturing agent of the present invention and the albumin denaturing composition of the present invention may be either liquid, powder, solid or the like, for example. The content of the quaternary ammonium in the albumin denaturing agent of the present invention is not limited particularly, but may be set to have a concentration that is necessary when being added to a sample, a reaction liquid and the like described below.

As described above, the albumin digesting method of the present invention is characterized in that the protease treatment is performed with respect to the sample in the presence of the albumin denaturing agent of the present invention or the albumin denaturing composition of the present invention, as described above.

In the present invention, an order of adding the albumin denaturing agent or the albumin denaturing composition of the present invention into the sample is not limited particularly, and it may be added, for example, before the adding of the protease, at the same time of the adding of the protease or after the adding of the protease. Moreover, the albumin denaturing compound of the present invention may include a protease.

Examples of the protease include metalloprotease, serine protease, serine carboxypeptidase, proteinase K, bromelain, papain, trypsin derived from porcine pancreas, a protease derived from *Bacillus subtilis*, a protease derived from *Aspegillus oryzae* and the like, and endoprotease preferably is used. Commercially available products that can be used for the protease include, for example, metalloprotease (produced by ARKRAY, Inc.), protease A "Amano" G (produced by Amano Enzyme Inc.), protease M "Amano" G (produced by Amano Enzyme Inc.), protease S "Amano" G (produced by Amano Enzyme Inc.), peptidase R (produced by Amano Enzyme Inc.), papain M-40 (produced by Amano Enzyme Inc.), protease N (produced by Fluka Chemie AG), protease N "Amano" (produced by Amano Enzyme Inc.), metalloproteinase derived from the genus *Bacillus* (produced by Toyobo Co., Ltd., product name: Toyoteam) and the like.

An adding ratio of the quaternary ammonium with respect to the reaction liquid of the protease treatment is not limited particularly, and ranges, for example, from 0.02 mmol/L to 20 mmol/L, and preferably ranges from 0.1 mmol/L to 3 mmol/L. An adding ratio of the quaternary ammonium per 1 mL of a blood plasma sample ranges, for example, from 0.003 mmol/L to 4 mmol/L, and preferably ranges from 0.015 mmol/L to 0.6 mmol/L. Incidentally, the contents of the quaternary ammonium in the albumin denaturing agent of the present invention and the albumin denaturing composition of the present invention are not limited particularly as described above, and preferably are contents that can adjust the adding ratio of the quaternary ammonium in the reaction liquid of the protease treatment to be in the above-described ranges when being added into the sample.

An adding ratio of the protease in the reaction liquid ranges, for example, from 0.01 KU/L to 20,000 KU/L, preferably ranges from 1 KU/L to 1,600 KU/L, and more preferably ranges from 1 KU/L to 500 KU/L. An adding ratio of the protease in 1 ml of the blood plasma sample ranges, for example, from 1 KU to 8,000 KU, preferably ranges from 1 KU to 240 KU, more preferably ranges from 1 KU to 60 KU, and further more preferably ranges from 1 KU to 35 KU. Here, KU represents $10^3 \times U$ (enzyme unit). The enzyme unit U may be an enzyme unit U provided by a manufacturer of the used protease, or may be an enzyme unit U that is defined such that 1 U is a protease activity degree showing coloration that corresponds to 1 μg of a tyrosine by digesting milk casein (for example, produced by MERCK JAPAN, LTD.) at 30° C. for 1 minute. That is, the protease solution appropriately is diluted with an appropriate enzyme diluent (for example, 20 mM an acetic acid buffer (pH 7.5), 1 mM calcium acetate, 100 mM sodium chloride) so as to have an enzyme unit U within a range, for example, from 10 U to 20 U, and 1 mL of this liquid is put into a test tube and is heated at 30° C. To this, 5 mL of a substrate (0.6% of milk casein) solution that is heated at 30° C. in advance is added. 5 mL of a reaction terminating liquid (0.11 M trichloroacetic acid, 0.22 M sodium acetate, 0.33 M acetic acid) is added after 10 minutes so as to terminate the reaction. Thereafter, the heating at 30° C. is continued for 30 minutes so as to aggregate a sediment, and is filtrated by a filter (for example, Toyo filter No. 131 (9 cm)) so as to obtain a filtrate. 5 mL of 0.55 M a sodium carbonate and 1 mL of a three-fold diluted Folins's reagent are added to 2 mL of this filtrate, and they react at 30° C. for 30 minutes. Thereafter, absorbance thereof at 660 nm is measured. By using this absorbance and a standard curve that separately is prepared by using a L-tyrosine, an enzyme activity degree of the protease is measured. As a result, an amount of the protease corresponding to the protease activity degree that shows coloration corresponding to 1 μg of a tyrosine by digesting the substrate (milk casein) at 30° C. for 1 minute can be defined as 1 U. Incidentally, in the case where the albumin denaturing composition of the present invention contains a protease, contents of the quaternary ammonium and the protease are not limited particularly as described above, and preferably are contents that are possible to adjust the adding ratios of the quaternary ammonium and the protease in the reaction liquid of the protease treatment to be in the above-described ranges when adding them into the sample.

Conditions for carrying out the protease treatment are not limited particularly, and a treating temperature ranges, for example, from 10° C. to 40° C., and preferably ranges from 25° C. to 37° C. A treating time (in particular, an upper limit thereof) is not limited, and for example, the protease treatment can be carried out in about 0.1 minutes to about 60 minutes, and preferably ranges, for example, from 0.5 minutes to 5 minutes. The method of the present invention can decrease an analyzing time to about a tenth or less of that in the conventional method in which the albumin denaturing agent (quaternary ammonium) of the present invention is not added.

The protease treatment preferably is carried out in, for example, a buffer solution, which may be a Tris-HCl buffer solution, an EPPS buffer solution, a PIPES buffer solution, a phosphate solution, an ADA buffer solution, a citrate buffer solution, an acetate acid buffer solution or the like. Moreover, the pH of the protease reaction liquid ranges, for example, 4 to 10, and for example, may be adjusted by the above-described buffer solutions.

During the protease treatment, besides the albumin denaturing agent of the present invention, the above-described compounds also may be present. The adding ratio of the compound is not limited particularly, but the following conditions are exemplified.

Next, as described above, the glycated albumin assaying method of the present invention includes: a step of digesting the albumin in the sample by the protease; a step of allowing the glycated part of the obtained digestion product of albumin to react with the FAOD; and a step of determining a ratio of the glycated albumin with respect to the albumin by measuring the redox reaction between the glycated part and the FAOD, which is characterized in that the sample is subjected to the protease treatment in the presence of the albumin denaturing agent of the present invention in the step of digesting the albumin.

The FAOD preferably is an enzyme that catalyzes a reaction in which hydrogen peroxide is generated using, for example, a glycated amine (for example, glycated amino acid and glycated peptide) of which an amino group (ϵ-amino group) in an amino acid side chain is glycated as a substrate. Such a catalytic reaction can be represented by the Formula (1) below, for example.

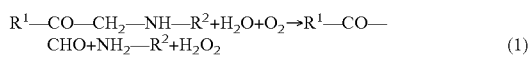
(1)

In Formula (1) above, $R^1$ represents a hydroxyl group or a residue derived from a sugar before glycation reaction (i.e., sugar residue). The sugar residue ($R^1$) is an aldose residue when the sugar before the reaction is an aldose, and it is a ketose residue when the sugar before the reaction is ketose. For example, when the sugar before the reaction is a glucose, it takes a fructose structure after the reaction by an Amadori rearrangement. In this case, the sugar residue ($R^1$) becomes a glucose residue (aldose residue). This sugar residue ($R^1$) can be represented, for example, by

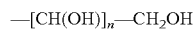

where n is an integer of 0 to 6.

In Formula (1), $R^2$ of the glycated amine of which the ϵ-amino group is glycated can be represented by Formula (2) below.

(2)

In Formula (2) above, $R^5$ represents a part of the amino acid side chain group except for the glycated amino group. For example, in the case where the glycated amino acid is a lysine, $R^5$ is represented by

and in the case where the glycated amino acid is an arginine, $R^5$ is represented by

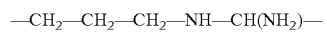

In Formula (2), $R^6$ represents a hydroxyl group, hydrogen, an amino acid residue or a peptide residue, and can be represented, for example, by Formula (3) below. In Formula (3), n is an integer of 0 or more, $R^3$ represents an amino acid side chain group as in the above, and the amino acid side chain groups may be either the same or different.

(3)

In Formula (2), $R^7$ represents a hydroxyl group, an amino acid residue or a peptide residue, and can be represented, for example, by Formula (4) below. In Formula (4), n is an integer of 0 or more, $R^3$ represents an amino acid side chain group as in the above, and the amino acid side chain groups may be either the same or different.

(4)

Incidentally, the FAOD of the present invention may have a catalytic function allowing a glycated amine of which an α-amino group is glycated, in addition to the glycated amine of which an ϵ-amino group is glycated that is represented by Formula (1) above, to be the substrate.

Examples of the FAOD that acts specifically on the glycated amine of which the ϵ-amino group is glycated (hereinafter, referred to as a "FAOD-S") include FAODs derived from the genus *Fusarium* ("Conversion of Substrate Specificity of Amino Acid Oxidase Derived from *Fusarium oxysporum*" by Maki FUJIWARA et al., Annual Meeting 2000, The Society for Biotechnology, Japan) and the like. Moreover, examples of a FAOD that acts on both of the glycated amine of which the ϵ-amino group is glycated and the glycated amine of which the α-amino group is glycated (hereinafter, referred to as a "FAOD-αS") include a commercially available product named FOD (produced by Asahi Chemical Industry Co., Ltd.), FAODs derived from the genus *Gibberella* (JP 8 (1996)-154672 A), FAODs derived from the genus *Fusarium* (JP 7 (1995)-289253 A), FAODs derived from the genus *Aspergillus* (WO 99/20039) and the like.

An embodiment of the glycated albumin assaying method of the present invention will be shown below, but the present invention is not limited to this.

Firstly, similarly to the above, an albumin containing sample is subjected to the protease treatment in the presence of the albumin denaturing agent of the present invention. A kind of the sample is not limited particularly, and may be, for example, a whole blood, a blood plasma, a serum, a hemolyzed sample or the like.

Then, the digestion product of the albumin obtained by the protease treatment is processed with the FAOD. Thereby, the FAOD acts on the glycated part of the ε-amino group in the digestion product of the albumin, and the hydrogen peroxide is generated as shown by above Formula (1).

The FAOD treatment preferably is performed in a buffer solution similarly to the protease treatment, and the buffer solution is not limited particularly, and a buffer solution similar to that of the protease treatment can be used. Conditions of the FAOD treatment are not limited particularly, pH of the reaction liquid ranges, for example, 6 to 9, and a treating temperature ranges, for example, from 10° C. to 38° C. and preferably ranges from 25° C. to 37° C. Also, a treating time is not limited particularly, and ranges, for example, from 0.1 minutes to 60 minutes, and preferably ranges from 0.1 minutes to 5 minutes.

An adding ratio of the FAOD in the reaction liquid for the FAOD treatment ranges, for example, from 0.01 KU/L to 50 KU/L, and preferably ranges from 0.2 KU/L to 10 KU/L. Moreover, an adding ratio of the FAOD in 1 mL of the blood plasma ranges, for example, from 0.01 KU to 10 KU, and preferably ranges from 0.04 KU to 1.5 KU.

Next, the redox reaction between the glycated part of the digestion product of albumin and the FAOD is measured. The measurement of this redox reaction can be carried out by measuring, for example, an amount of hydrogen peroxide generated by the reaction represented by above Formula (1) or an amount of oxygen consumed by the reaction.

The hydrogen peroxide amount can be calculated by using, for example, a substrate that develops a color by oxidation with a peroxidase (POD) (hereinafter, referred to as a "chromogenic substrate"), developing the color of the chromogenic substrate by the reaction thereof with the generated hydrogen peroxide, and measuring a level of this color. Incidentally, the hydrogen peroxide amount also can be measured not only by an enzymatic method using the POD or the like, but also by an electric method.

The above-noted substrate that develops the color by oxidation (chromogenic substrate) is not particularly limited, and can be, for example, 10-(carboxymethylaminocarbonyl)-3,7-bis(dimethylamino)phenothiazine or its salt (for example, product named DA-67, Wako Pure Chemical Industries, Ltd.), N,N,N',N',N'',N''-hexa(3-sulfopropyl)-4,4',4''-triaminotriphenylmethane hexasodium salt (for example, product named TPM-PS, manufactured by DOJINDO LABORATORIES), N-(carboxymethylaminocarbonyl)-4,4-bis(dimethylamino) diphenylamine sodium, orthophenylendiamin (OPD), a substrate of a combination of Trinder's reagent and 4-aminoantipyrine or the like. The Trinder's reagent can be, for example, phenols, phenol derivatives, aniline derivatives, naphthols, naphthol derivatives, naphthylamine, naphthylamine derivatives or the like. Other than the 4-aminoantipyrine noted above, it also is possible to use aminoantipyrine derivatives, vanillin diamine sulfonic acid, methylbenzothiazolinone hydrazone (MBTH), sulfonated methyl benzothiazolinone hydrazone (SMBTH) or the like. Among them, 10-(carboxymethylaminocarbonyl)-3,7-bis(dimethylamino)phenothiazine and TPM-PS are preferable, because pigmentation of them caused by the oxidation is not likely to be extinguished even by the reducing power of the above-described quaternary amine.

The POD reaction preferably is effected in the buffer solution similarly to that in the protease treatment, and the above-described buffer solutions can be used. Conditions of the POD treatment are not limited particularly, and a pH of the reaction liquid ranges, for example, from 5 to 9, and a treating temperature ranges, for example, from 10° C. to 40° C., and preferably ranges from 25° C. to 37° C. Also, a treating time is not limited particularly, and ranges, for example, from 0.1 minutes to 5 minutes.

An adding ratio of the POD in the POD reaction liquid ranges, for example, from 0.01 KU/L to 600 KU/L. Moreover, an adding ratio of the chromogenic substrate in the reaction liquid ranges, for example, from 0.001 mmol/L to 10 mmol/L, and preferably ranges from 0.001 mmol/L to 2 mmol/L.

In the case of using the chromogenic substrate as described above, for example, the developed color (for example, absorbance of the reaction liquid) may be measured by a spectrophotometer. Since the hydrogen peroxide amount corresponds to the glycation amount of the albumin (glycated albumin amount), a glycated albumin concentration can be calculated from the measured absorbance. Then, a ratio (%) of the glycated albumin concentration with respect to the total albumin concentration in the sample can be calculated from the below formula. This ratio can be represented as GA (%) generally. Incidentally, the albumin amount (concentration) can be measured by a conventionally known method by using a commercially available reagent kit.

$$GA(\%) = (\text{glycated albumin concentration/albumin concentration}) \times 100$$

The glycated albumin concentration can be calculated from the absorbance, by using a standard curve obtained by plotting a relationship between the known glycated albumin amount and the absorbance. For example, absorbance of an albumin reference solution whose glycated albumin amount is known is measured similarly to the above, and a standard curve showing a relationship between the measurement value of this reference solution and the known glycated albumin amount is formed. Then, the absorbance measured as described above is substituted into this standard curve, thereby calculating the glycated albumin concentration.

In the above-described assay of a glycation degree of the present invention, respective treating steps may be carried out separately as described above, and may be carried out at the same time, for example, in combinations described below. Also, the order of adding the protease, the FAOD, the POD and the chromogenic substrate are not limited particularly.

1: protease treatment+FAOD treatment of digestion product of albumin

2: FAOD treatment+POD treatment

3: protease treatment+FAOD treatment+POD treatment

Moreover, in the glycated albumin assaying method of the present invention, in order to suppress the effect of other protein, for example, before adding the albumin denaturing agent of the present invention or the albumin denaturing composition of the present invention, the protease and the FAOD may be added into the sample (the POD further may be added thereto) so as to perform the protease treatment and the FAOD treatment as pretreatment. If other glycated protein is present in the sample, the other glycated protein also is digested by the protease treatment, the FAOD acts on the thus obtained digestion product so as to generate hydrogen peroxide, and the amount of the generated hydrogen peroxide also is measured, so that a measurement error may occur. In such a case, if the sample is subjected to the pretreatment in advance, the albumin is denatured by the adding of a denaturing agent or the denaturing composition of the present invention, and other glycated protein is already treated by the pretreating protease and the pretreating FAOD before accelerating the digestion, so that the effect of other glycated protein can be suppressed.

The processing protease and the albumin digesting protease may be the same or different in kind. In the case of using the same kinds of proteases, it is possible to add them into the sample separately for the pretreatment and for the albumin, and also is possible to add the protease for the pretreatment, leave it still for a certain period of time for allowing it to act on other protein, and add the albumin denaturing agent of the present invention or the albumin denaturing composition of the present invention without further adding the protease so as to accelerate the albumin digestion. Moreover, in the case of using the different kind of proteases, for example, a protease for selectively digesting other glycated protein also may be used for the pretreatment. The FAODs are preferably the same in kind, and the FAODs added for the pretreatment may be used directly so as to react with the digestion product of albumin, and also may be added separately for the pretreatment and for treating the digestion product of albumin.

In order to simply achieve the glycated albumin assaying method of the present invention, the albumin denaturing agent, the enzyme, the substrate and the like described above can be made into kits as a plurality of mixed reagents. Table 1 described below will exemplify combinations of the mixed reagents, but the present invention is not limited to them. Incidentally, the respective reagents may be added into the sample in the order of the numbers (first>>second). As listed in Table 1 below, the albumin denaturing composition of the present invention can be either a first reagent (Combination 2) or a second reagent (Combinations 1, 3 to 5).

TABLE 1

| Combination | First reagent | Second reagent |
|---|---|---|
| (1) | FAOD + POD | protease + chromogenic substrate + quaternary ammonium |
| (2) | protease + quaternary ammonium | FAOD + POD + chromogenic substrate |
| (3) | protease + FAOD + POD | quaternary ammonium + chromogenic substrate |
| (4) | protease + FAOD | POD + quaternary ammonium + chromogenic substrate |
| (5) | protease | FAOD + POD + quaternary ammonium + chromogenic substrate |

Moreover, the quaternary ammonium that is the albumin denaturing agent of the present invention also can improve the stability of 10-(carboxymethylaminocarbonyl)-3,7-bis(dimethylamino)phenothiazine that is a chromogenic substrate or a salt thereof (for example, product name: DA-67, Wako Pure Chemical Industries, Ltd.) in a liquid state. Thus, it also is preferable to add the quaternary ammonium in the reagent containing the chromogenic substrate. Thereby, the stability of the chromogenic substrate can be improved, and the albumin is denatured by the addition of the quaternary ammonium into the sample so as to accelerate the albumin digestion by the protease.

The present invention will be described more specifically below by way of examples and comparative examples, but the present invention is not limited to them.

Example 1

A blood plasma sample is subjected to protease treatment in the presence of quaternary ammonium, thereby confirming an increase of an efficiency of albumin digestion.

<First Reagent: R1>

| | |
|---|---|
| Tricine | 50 mmol/L (pH 8) |
| FAOD (produced by ARKRAY, Inc., used also in the following examples) | 2.5 KU/L |
| POD | 2 KU/L |

<Second Reagent: R2>

| | |
|---|---|
| additive | 0.2 g/L |
| metalloproteinase (produced by ARKRAY, Inc., used also in the following examples) | 1300 KU/L |
| chromogenic reagent (product name: DA-67, produced by Wako Pure Chemical Industries) | 0.05 mmol/L |

<Additive to be Added into Second Reagent>

Example stearyltrimethylammonium chloride[1] (produced by NACALAI TESQUE, INC.)
stearyltrimethylammonium chloride[2] (product name: CORTAMINE 86P conc, produced by Kao Corporation)
cetyltrimethylammonium bromide
hexadecyltrimethylammonium bromide
benzalkonium chloride
benzyldimethyltetradecylammonium chloride
benzethonium chloride
myristyltrimetylammonium bromide (produced by NACALAI TESQUE, INC.)
coconut amine acetate (product name: ACETAMIN 24, produced by Kao Corporation)
lauryltrimethylammonium chloride (product name: CORTAMINE 24P, produced by Kao Corporation)
lauryltrimethylammonium bromide Comparative Example benzyltriethylammonium bromide
benzyltrimethylammonium bromide
tetraethylammonium chloride
AMIPOL (betaine type ampholytic surfactant) (product name: AMIPOL, produced by NICCA CHEMICAL CO., LTD.)

<Blood Plasma Sample>

A blood plasma of a normal subject is diluted with purified water at predetermined dilution ratios (0-fold, two-fold, four-fold), thereby preparing samples. According to the contents of the blood plasma in the samples, the non-diluted sample is shown as "1.0", the two-fold sample is shown as "0.5", the four-fold sample is shown as "0.25", and the purified water as a control is shown as "0".

<Assaying Method>

1.2 μL of the blood plasma and 78 μL of the first reagent (R1) was mixed and was incubated at 37° C. for 5 minutes, and thereafter, 26 μL of the second reagent (R2) further was added thereto, which were subjected to the protease treatment at 37° C. and effected the chromogenic reactions. Then, absorbance ($A_0$) at a wavelength of 658 nm in reaction liquids immediately before adding the second reagent and absorbance ($A_5$) at a wavelength of 658 nm in the reaction liquids after 5 minutes from the adding of the second reagent were measured with the biochemical automatic analyzer (product name: JCA-BM8, produced by JEOL Ltd., used also in the following examples), and differences therebetween ($A_5$-$A_0$) were obtained. Results will be shown in Table 2 below. Moreover, a change of the absorbance over time in the case of using stearyltrimethylammonium chloride as the second reagent is shown in FIG. 1.

TABLE 2

| Second reagent | | Sample | | | |
|---|---|---|---|---|---|
| | | 0 | 0.25 | 0.5 | 1.0 |
| Additive compound | Carbon number | Purified water | Four-fold | Two-fold | Non-diluted |
| <Control> | | | | | |
| control-free | | 0.000 | −0.002 | −0.004 | 0.001 |
| <Example 1> | | | | | |
| stearyltrimethyl-ammonium chloride*[1] | 17 | 0.000 | 0.017 | 0.024 | 0.050 |
| stearyltrimethyl-ammonium chloride*[2] | 17 | 0.000 | 0.011 | 0.023 | 0.046 |
| cetyltrimethyl-ammonium bromide | 16 | 0.000 | 0.015 | 0.021 | 0.045 |
| hexadecyltrimethyl-ammonium bromide | 16 | 0.000 | 0.014 | 0.019 | 0.043 |
| benzalkonium chloride | 8-18 mixture | 0.000 | 0.012 | 0.017 | 0.044 |
| benzyldimethyl-tetradecylammonium chloride | 14 | 0.000 | 0.012 | 0.016 | 0.042 |
| benzethonium chloride | 14 | 0.000 | 0.010 | 0.018 | 0.049 |
| myristyltrimetyl-ammonium bromide | 14 | 0.000 | 0.008 | 0.012 | 0.033 |
| coconut amine acetate | 8-18 mixture | 0.000 | 0.005 | 0.013 | 0.038 |
| lauryltrimethyl-ammonium chloride | 12 | 0.000 | 0.006 | 0.014 | 0.026 |
| lauryltrimethyl-ammonium bromide | 12 | 0.000 | 0.005 | 0.006 | 0.024 |
| <Comparative Example 1> | | | | | |
| benzyltriethyl-ammonium bromide | 6 | 0.000 | 0.003 | −0.003 | −0.001 |
| benzyltrimethyl-ammonium bromide | 6 | 0.000 | 0.003 | −0.002 | 0.000 |
| tetraethylammonium chloride | 5 | 0.000 | 0.003 | −0.001 | −0.002 |
| AMIPOL | | 0.000 | 0.001 | 0.004 | 0.003 | unit: ΔAbs

As shown in Table 2 above, it can be seen that, in Example 1 using a quaternary ammonium salt having a hydrocarbon group with a carbon number of 12 or more, the albumin is digested further more efficiently than that of Comparative Example 1 using other quaternary ammonium or a surfactant. Moreover, in Comparative Example 1, almost no difference was found in absorbance between the kinds of the blood plasma samples (contents of the blood plasma). On the other hand, Example 1 achieved the result that higher absorbance was shown as the dilution ratio is lower, that is, the blood plasma content in the sample is higher, which shows a correlation between the blood plasma content in the sample and the increase of the absorbance. From this result, it is found that, according to the quaternary ammonium of Example 1, the albumin was denatured, and was digested by the protease efficiently. Further, as shown in FIG. 1, in the example using the stearyltrimethylammonium chloride, the absorbance was increased immediately after the adding of the second reagent, more than that of the control. That is, when adding the quaternary ammonium, the digestion by the protease starts promptly. From this fact, the timing for adding the quaternary ammonium is not limited particularly, as long as the quaternary ammonium is present with the protease at the time of the protease treatment.

Comparative Example 2

Further, by using various kinds of surfactants (listed in Table 3 below) as the additive, the increase of the efficiency of the albumin digestion by the protease was confirmed.

<First Reagent>

| MOPS | 30 mmol/L (pH 7.5) |
|---|---|
| FAOD | 10 KU/L |
| POD | 2 KU/L |
| surfactant | 2 g/L or 10 g/L |

<Second Reagent>

| metalloproteinase | 10,000 KU/L |
|---|---|
| chromogenic reagent (product name: TPM-PS, produced by Dojindo Laboratories) | 0.05 mmol/L |
| $CaCl_2$ | 5 mmol/L |
| MOPS | 150 mmol/L (pH 7.5) |

<Blood Plasma Sample>

A blood plasma of a normal subject is diluted with purified water at predetermined dilution ratios (0-fold, four-thirds-fold, two-fold, four-fold), thereby preparing samples. According to the contents of the blood plasma in the samples, the non-diluted sample is shown as "1.0", the two-fold sample is shown as "0.5", the four-thirds-fold sample is shown as "0.75", the four-fold sample is shown as "0.25", and the purified water as a control is shown as "0".

<Assaying Method>

1.2 μL of the blood plasma and 78 μL of the first reagent were mixed and were incubated at 37° C. for 5 minutes, and thereafter, 26 μL of the second reagent further was added thereto, which were incubated at 37° C. for 5 minutes. Then, absorbance ($A_0$) at a wavelength of 658 nm in reaction liquids immediately before adding the second reagent and absorbance ($A_5$) at a wavelength of 658 nm in the reaction liquids after 5 minutes from the adding of the second reagent were measured with the biochemical automatic analyzer, and differences therebetween ($A_5$-$A_0$) were obtained. Results will be shown in Table 3 below.

TABLE 3

| Additive | | Sample | | | | |
|---|---|---|---|---|---|---|
| | | 0 | 0.25 | 0.5 | 0.75 Four-thirds-fold | 1.0 |
| Kind of surfactant | Concentration | Purified water | Four-fold | Two-fold | | Non-diluted |
| <Control> | | | | | | |
| control-free | | 0.000 | 0.003 | 0.004 | 0.005 | 0.007 |
| <Example 1> | | | | | | |
| Product name: Synperonic | 10 g/L | 0.000 | 0.000 | 0.002 | 0.004 | 0.005 |
| | 2 g/L | 0.000 | 0.001 | 0.003 | 0.004 | 0.007 |

TABLE 3-continued

| Additive | | Sample | | | | |
|---|---|---|---|---|---|---|
| Kind of surfactant | Concentration | 0<br>Purified water | 0.25<br>Four-fold | 0.5<br>Two-fold | 0.75<br>Four-thirds-fold | 1.0<br>Non-diluted |
| Product name: PE L64 | 2 g/L | 0.000 | 0.000 | 0.001 | 0.003 | 0.004 |
| Product name: Amps-58 | 10 g/L | 0.000 | 0.002 | 0.003 | 0.004 | 0.006 |
| Product name: Amps-X100 | 2 g/L | 0.000 | 0.001 | 0.003 | 0.005 | 0.007 |
| | 10 g/L | 0.000 | 0.002 | 0.002 | 0.003 | 0.004 |
| Product name: EMULGEN A60 | 2 g/L | 0.000 | 0.001 | 0.003 | 0.004 | 0.005 |
| | 10 g/L | 0.000 | 0.001 | 0.002 | 0.004 | 0.005 |
| Product name: Brij 98 | 2 g/L | 0.000 | 0.002 | 0.003 | 0.004 | 0.005 |
| Product name: Tween20 | 2 g/L | 0.000 | 0.002 | 0.003 | 0.004 | 0.006 |
| Product name: MEGA 8 | 2 g/L | 0.000 | 0.002 | 0.004 | 0.005 | 0.005 |
| | 10 g/L | 0.000 | 0.003 | 0.003 | 0.003 | 0.001 |
| Product name: DCHP | 2 g/L | 0.000 | 0.002 | 0.004 | 0.005 | 0.006 |
| | 10 g/L | 0.000 | 0.000 | 0.003 | 0.004 | 0.005 |
| Product name: Pluronic F88 | 2 g/L | 0.000 | 0.000 | 0.002 | 0.003 | 0.008 |
| cholic acid | 2 g/L | 0.000 | 0.002 | 0.003 | 0.005 | 0.004 | unit: ΔAbs

As shown in Table 3 above, even when the various kinds of the surfactants coexist with the protease, the increase of the efficiency of the albumin digestion was not observed.

INDUSTRIAL APPLICABILITY

As described above, according to the albumin denaturing agent of the present invention, the albumin can be digested efficiently by the protease treatment in the presence of the albumin denaturing agent. Thus, the sufficient albumin digestion can be realized by, for example, a small amount of the protease, and the conventional problems caused by using a large amount of the protease can be avoided. Thus, according to the albumin digesting method and the glycated albumin assaying method of the present invention using such an albumin denaturing agent, the glycated albumin can be assayed more efficiently than conventional methods, and the methods of the present invention are significantly useful in the medical field such as diagnoses, treatment and the like of diabetes.

The invention claimed is:

1. A method for assaying glycated albumin, comprising:
    adding a metalloprotease into a sample containing the glycated albumin so as to digest the glycated albumin with the metalloprotease;
    adding quaternary ammonium having a hydrocarbon group with a carbon number of 14 or more, or a salt of the quaternary ammonium before, at the same time of or after the adding of the metalloprotease, wherein a resultant concentration of the metalloprotease ranges from 1 KU/L to 1,600 KU/L,
    adding a fructosyl amino acid oxidase (FAOD) to the sample so that a glycated part of the digestion product of the glycated albumin reacts with the FAOD, wherein the FAOD is added before, at the same time or after the adding of the metalloprotease;
    measuring an amount of a redox reaction product generated by a redox reaction between the glycated part of the digestion product of the glycated albumin and the FAOD; and
    correlating the measured amount of the redox reaction product with an amount of the glycated albumin in the sample.

2. A method for assaying glycated albumin, comprising:
    adding a metalloprotease into a sample containing the glycated albumin so as to digest the glycated albumin with the metalloprotease;
    adding quaternary ammonium having a hydrocarbon group with a carbon number of 14 or more, or a salt of the quaternary ammonium before, at the same time of or after the adding of the metalloprotease, wherein an adding amount of the metalloprotease ranges from 1 KU to 60 KU in 1 ml of the sample;
    adding a fructosyl amino acid oxidase (FAOD) to the sample so that a glycated part of the digestion product of the glycated albumin reacts with the FAOD, wherein the FAOD is added before, at the same time or after the adding of the metalloprotease;
    measuring an amount of a redox reaction product generated by a redox reaction between the glycated part of the digestion product of the glycated albumin and the FAOD; and
    correlating the measured amount of the redox reaction product with an amount of the glycated albumin in the sample.

3. The method of claim 1, wherein the redox reaction product measured is hydrogen peroxide, wherein measuring the amount of the redox reaction product includes adding a peroxidase and a chromogenic substrate to the sample so that the hydrogen peroxide reacts with the chromogenic substrate, and measuring a chromogenic level of the chromogenic substrate, and wherein correlating the measured amount of the redox reaction product with an amount of the glycated albumin includes calculating the amount of the glycated albumin based on the measured chromogenic level of the chromogenic substrate.

4. The method of claim 2, wherein the redox reaction product measured is hydrogen peroxide, wherein measuring the amount of the redox reaction product includes adding a peroxidase and a chromogenic substrate to the sample so that the hydrogen peroxide reacts with the chromogenic substrate, and measuring a chromogenic level of the chromogenic substrate, and wherein correlating the measured amount of the redox reaction product with an amount of the glycated albumin includes calculating the amount of the glycated albumin based on the measured chromogenic level of the chromogenic substrate.

* * * * *